United States Patent [19]
Balko et al.

[11] Patent Number: 4,512,338
[45] Date of Patent: Apr. 23, 1985

[54] PROCESS FOR RESTORING PATENCY TO BODY VESSELS

[76] Inventors: Alexander B. Balko, 30 Red Barn La., East Greenwich, R.I. 02818; Dhiraj M. Shah, R.D. #1, Rte. 43, Rensselaer, N.Y. 12144

[21] Appl. No.: 460,842

[22] Filed: Jan. 25, 1983

[51] Int. Cl.³ .................... A61M 29/00; A61B 19/00
[52] U.S. Cl. ................................. 128/1 R; 128/341
[58] Field of Search .................. 3/1.4; 128/341, 343, 128/345; 604/8; 128/1 R

[56] References Cited
U.S. PATENT DOCUMENTS 3,868,956 3/1975 Alfidi et al. .................. 128/345
4,170,990 10/1979 Baumgart et al. ............ 128/92 B
4,425,908 1/1984 Simon .......................... 128/325

Primary Examiner—C. Fred Rosenbaum
Assistant Examiner—C. W. Shedd
Attorney, Agent, or Firm—Robert J. Doherty

[57] ABSTRACT

A process in which a shape memory alloy such as nitinol wire which has been previously fabricated in its parent phase to form a longitudinally oriented coil of adjacent wire loops and thereafter cooled to its martensite phase and reshaped to a relatively straight shape, is utilized as an intra-luminal device to reinforce or replace a weakened or otherwise damaged vessel. The reformable wire is inserted into the vessel in such a manner to be temperature insulated such that upon the removal of the insulation means, the wire reforms to its coil shape so as to be urged against the internal walls of the damaged vessel and supplies a patent channel through which body fluids may pass. In this manner, removal of the damaged portion of the vessel with the attachment of graft material as a replacement thereto along with the complex surgical techniques required to perform such is avoided.

15 Claims, 8 Drawing Figures

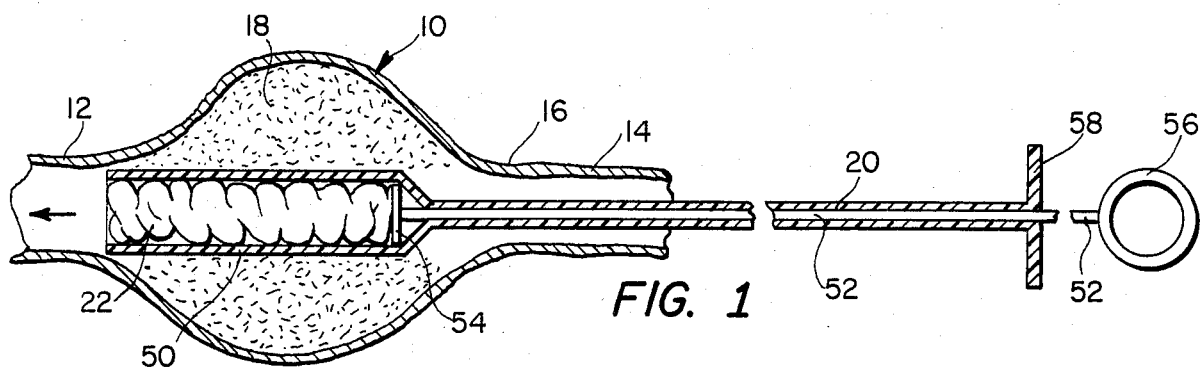
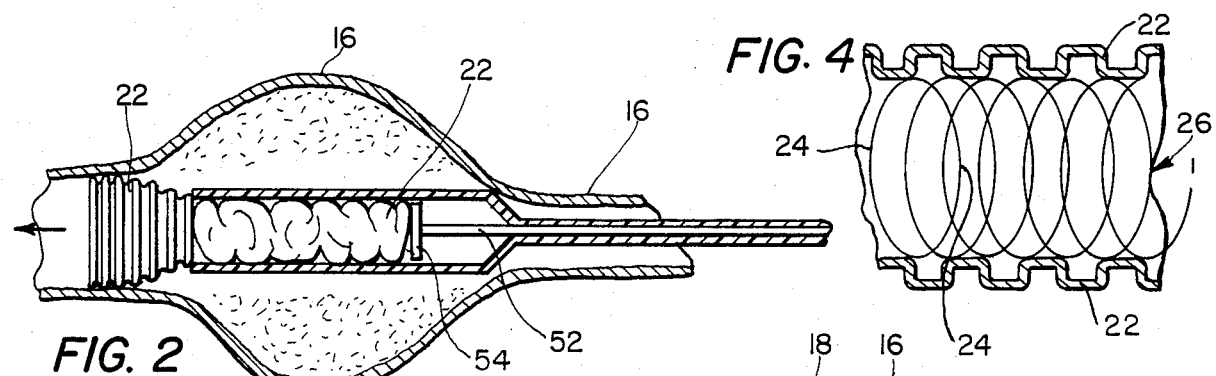
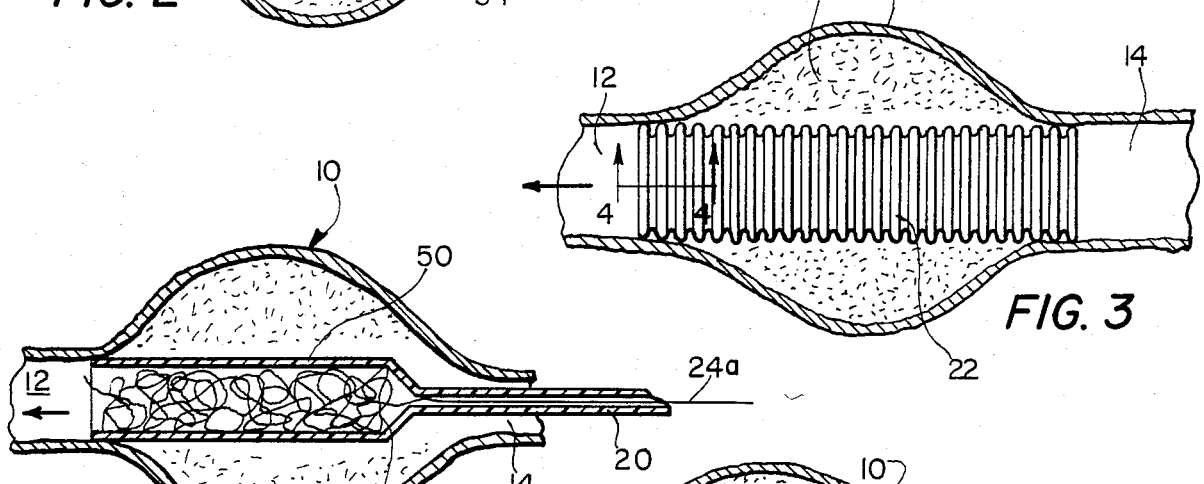
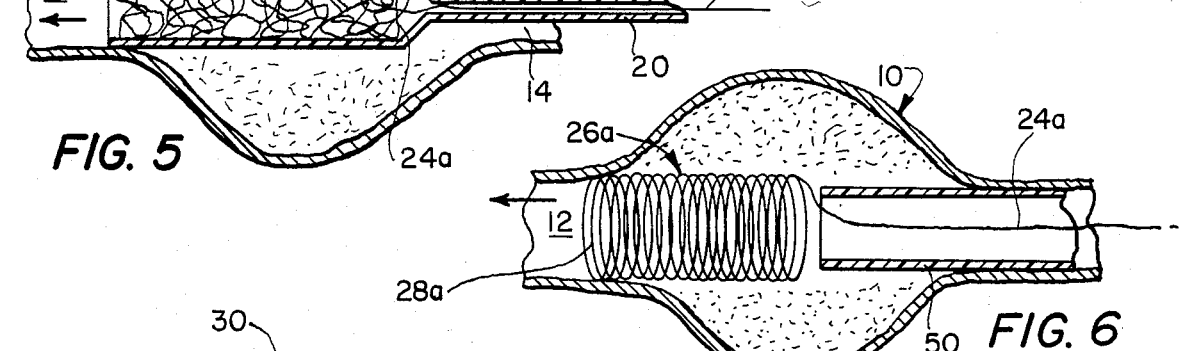
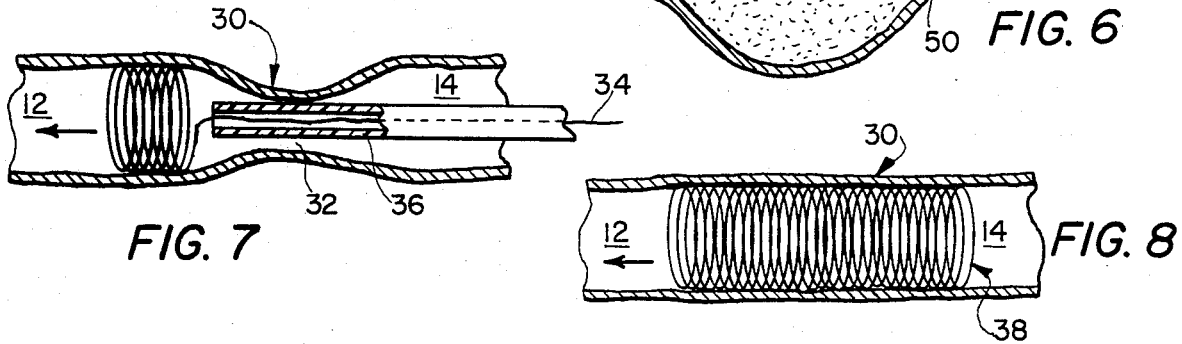

PROCESS FOR RESTORING PATENCY TO BODY VESSELS

BACKGROUND AND OBJECTS OF THE INVENTION

This invention deals with improved methods of treating defects in body vessels. It has use in patient trauma caused by a gunshot wound, stabbing, etc. or where the vessel (artery, vein, or other body passage) is perforated or disrupted. It is also particularly adapted but not limited to reconstruction of an abdominal aortic aneurysm.

Presently such aneurysms are surgically corrected by the re-section thereof with accompanying installation of a replacement graft. Generally this graft is of a Dacron material constructed in longitudinally expandible tubular form and is surgically connected between the remaining portion of the aorta and the left and right iliac arteries. Such procedure is in detail described in an article set forth on FIGS. 1 through 20, Pages 231 through 233 entitled "Resection of Abdominal Aortic Anerurysm" published in the *Atlas of Surgical Operations*, 4th ed. R. M. Zollinger and R. M. Zollinger, Jr.. Such procedure is time consuming, requires high skill and involves a significant amount of patient risk. Accordingly, it would be highly desirable to replace such technique with a simpler, less traumatic procedure which is, accordingly, the primary object of the present invention.

These and other objectives of the present invention are accomplished by the use of a wire alloy coil for having shape memory characteristics. The wire in non-coil form is positioned in the weakened vessel such that upon reformation by an increase in temperature to the coil form enables the coil to bridge the weakened vessel portion so as to form a substitute vessel wall portion in that defective area. More specifically, the process involves a reduced or non-surgical restoration of the patency of a hollow body vessel which includes a localized defect disposed intermediate first and second potent vessel portions, comprising inserting at least the front end of a continuous length of shape-memory alloy wire which has been previously fabricated in its parent phase to form a longitudinally oriented coil of adjacent wire loops and then cooled to its martensite phase and reshaped to a relatively straight length along the interior of said vessel past said defect to a position adjacent the first potent vessel portion while maintaining the temperature of said wire below its martensite transformation point and thereafter heating said wire to its transformation point progressively from the front thereof to the rear thereof so as to initially cause the thus reshaped wire loops of the front wire end to be urged against the interior of said first potent vessel portion so as to be at least temporarily positioned thereat and thereafter cause the reformation of the remainder of said coil so as to bridge said localized defect and into position adjacent said second potent vessel portion.

Other objects, features and advantages of the invention shall become apparent as the description thereof proceeds when considered in connection with the accompanying illustrative drawing.

DESCRIPTION OF THE DRAWING

In the drawing which illustrates the best mode presently contemplated for carrying out the present invention:

FIG. 1 is a partial sectional view showing the restoration of a body vessel, namely, the aorta having an aneurysm therein with the procedure and devices of the present invention in an initial stage;

FIG. 2 is a view similar to FIG. 1 but showing an intermediate stage after the wire has been heated and has started to form a coil;

FIG. 3 shows the completed procudure;

FIG. 4 is a partial sectional view taken through line 4—4 of FIG. 3;

FIG. 5 is a view similar to FIG. 1 but showing a modified form of the invention wherein a fabric graft is not utilized;

FIG. 6 is a view similar to FIG. 2 but showing an intermediate step in the procedure shown in FIG. 5;

FIG. 7 is a partial sectional view of another form of the invention in a partially completed stage; and FIG. 8 is a view similar to FIG. 7 but showing the completed repair structure.

DESCRIPTION OF THE INVENTION

Turning now to the drawing and more particularly FIGS. 1 through 3, 5, and 6 thereof, the present invention will be explained in relationship to the repair of an aortic aneurysm. It should be brought out, however, that the present invention has utility not only as a reinforcement of a weakened arterial wall such as the aortic aneurysm shown but also in the restoration of patency to previously narrowed, weakened, ballooned, or otherwise defective or imparied lumen or other body channels. Such body channels may include arteries, the esophagus, bile ducts, urethra, trachea and the like. Other specific uses to which the procedures described in the present invention include the repair or correction of the following: intraluminal lining of AAA or iliac or femoral aneurysms; recanalization of injured vessels caused by blunt or penetrating trauma; dilation and recanalization of stenotic arterial segments; tampanade and obliteration of bleeding esophageal varices; recanalization of esophageal stenoses secondary to carcinoma or benign strictures; dilation and recanalization of coarctation of aorta; dilation and recanalization of biliary stenoses secondary to strictures, tumors and cancer of pancreas and common bile duct; ureteral strictures and tracheal strictures.

It should also be understood that the above use list is not intended to be exclusive and that any body vessel which has been narrowed, weakened, or in another way requires a reinforcement may be subject to the present invention. Also as utilized therein, the term vessel is used in a generic sense to include body channels including but not limited to artery, esophagus, bile duct, uretha, trachea, and the like and that the term body includes not only humans but animals as well.

One form of the present invention is illustrated in FIGS. 1 through 4 wherein an aortic aneurysm is shown being repaired by the procedure shown by the progressive drawing sequence of FIGS. 1 through 3. Therein an aneurysm 10 is depicted intermediate patent proximal or first and distal or second portions 12, 14 of the aorta 16. The lining of the aneurysm 10 includes clotted blood material or plaque 18 which in turn reduces the effective passage of arterial blood through the aorta and increases the chance of clotted material entering the blood stream and causing damage elsewhere in the body.

A hollow sheath 20 is shown inserted as by conventional techniques into the aorta 16 from the distal side thereof as pictured to the right of FIG. 1 and positioned so as to be adjacent the proximal side of the aneurysm 10 but well within the patent portion 12 thereof (distal and proximal refer to positioning relative to the heart, that is, remote from and close to respectively). In this regard, an arrow pointing towards the position of the patient's heart has been placed at the proximal side in each drawing figure. A fabric graft 22 is positioned within the sheath 20 and is selected of an adequate longitudinal extent so as to adequately span the aneurysm 10, that is, to contact patent vessel portions 12 and 14 on opposite sides of such aneurysm. The sheath 20 may include an enlarged proximal end 50 to accomodate the folded or bunched together, etc. graft structure 22. Such graft 22 may take the form of those currently utilized in full surgical techniques such as previously referred to in the Zollinger et al publication and utilized to at least in part illustrate the state of the prior art prior to the present invention. Such Dacron or other synthetic or natural material graft may be accordian pleated such that its overall length is shortened when introduced, then expanded as will hereinafter be more fully explained so as to span the full extent of the aneurysm.

A shape memory metal alloy wire is attached to the graft 22 at least at its proximal end and may be attached at a plurality of longitudinally spaced locations along such graft. The wire 24 is of an alloy such as Nitinol which exhibits anthropomorphic qualities of memory and trainability and are commonly referred to as shape-memory alloys. If such alloys are plastically deformed at one temperature, they will completely recover to their original shape on being raised to a higher temperature. A discussion and identification of such alloys is set forth in the article by L. McDonald Shetky entitled "Shape-Memory Alloys" at Pages 74 through 82 of Vol. 241 (5) Nov. 1979 *Scientific American* a copy of which is attached hereto and specifically incorporated into this specification by specific reference thereto. A further discussion of such alloys and particularly nickel-titanium alloys commonly referred to as nitonol is set forth in the publication "A Source Manual for Information on Nitonol and NiTi", First Revision, by David Goldstein, Research and Technology Department, Feb. 1 1980, Naval Surface Weapons Center, Dahlgren, Va. 22448 (NSWC TR 80-59), a copy of which is attached hereto and specifically incorporated into this specification by specific reference thereto.

In the present invention, a Nitinol wire 24 which has been alloyed to exhibit a martensite transformation temperature somewhat below the normal body temperature range is satisfactory. Such wire is shaped by known techniques into the form of a continuous coil. The individual loops 28 are disposed in adjacent but spaced relationship to each other while in a parent phase and thereafter cooled so as to produce a martensite crystaline form and thereafter reshaped so as to form a relatively straight length of continuous wire. The wire 24 is maintained in such condition by maintaining the temperature thereof below its martensite transformation temperature of approximately 37° in this case. The manner in which said wire is attached to the graft 22 may be by conventional techniques such as sewing and the like.

In this regard, it should be pointed out that when the wire resumes its coiled form after being internally positioned in the body vessel, in this case the aorta 16, it will if appropriately attached to the graft 22 expand such graft longitudinally. Accordingly, a leading portion of the wire 24 is attached to the graft and thereafter if desired at points along the length of the wire such that several continuous loops may be formed therebetween such attachment points. The wire intermediate such attachment points may be compressed or bunched so as to be conveniently housed within the proximal portion 50 of the insulating sheath 20.

Such sheath 20 is preferably formed of an insulating plastic resinous material such as polyethylene and the like and is of sufficient thickness so as to maintain the temperature of the wire 24 below its martensite transformation point during the insertion of the sheath into the desired position within the aorta. Such position is upstream of the aneurysm 10 (proximal to the heart) and generally adjacent thereto but well within the extent of the first patent portion 12 of the aorta 16. Thereafter, the sheath 20 is initially withdrawn a short distance so as to expose a portion of the lead portion of the wire and graft 22 such that the wire is exposed to the heat of the surrounding body tissue and permitted to reach and exceed the martensite transformation phase and, accordingly, initiate reformation into its coiled form. In this regard, it should be pointed out that the diameter of the coil as initially formed is approximately equal to or slightly greater than that of the normal internal diameter of the patent aorta portions 12 and 14 such that the individual loops 28 of the coil 26 urge the graft material 22 snuggly against the patent portions of the aorta 16 so as to insure a positive position therein as shown in FIG. 2. Thereafter the remainder of the insulation sheath is progressively removed such that the entire reformation of the coil takes place with the attendant longitudinal extension of the graft 22. The interior of the sheath may be fitted with a relatively stiff member 52, i.e., a wire or rod-like element, having a platform 54 attached at its proximal end and positioned within the enlarged sheath head 50. The member 52 may include a thumb ring 56 at its distal end such that the surgeon may more easily manipulate and thus position the sheath 20 as by inserting his or her thumb through ring 56 and grasping the distal end of the sheath 20 by a flange 58 provided thereat.

Also the diameter of the coil is preferably such that it approximates the normal internal extent of the aorta such that the passage of blood therethrough may be normal. Also where appropriate, the flow of blood through the aorta is temporarily shunted by conventional means such as the insertion of an inflatable catheter if required or desirable in regard to the heating and shaping memory characteristics of the wire 24 or to assist in the initial positioning and/or expansion of the wire.

It may thus be seen that the overall objectives of the present invention are carried out by the above-described novel procedure and such is accomplished without full surgical techniques and with a minimum possibility of dislodging clotted material from the aneurysm 10 into the blood stream.

Turning now to FIGS. 5 and 6 of the drawing, a modified form of the invention is shown wherein the fabric graft 22 of the previously described embodiment has been omitted. In that regard, the formation of the coil 26a is such that the individual loops 28a thereof are very closely spaced so as to approach or actually physically touch each other. Otherwise, the procedure as previously described in the embodiment of FIGS. 1 through 4 is essentially the same, that is, an insulating sheath 20 carrying the wire 24a is projected into the vessel and thereafter the sheath slightly withdrawn such that the wire initially expands into a partial coil form and to directly contact the internal surface of the first patent aorta portion 12 and thereafter progressively withdrawn so as to bridge the aneurysm 10 in the same manner as previously described and thereafter come into positioning contact with the second patent portion 14. The wire in this embodiment need not, however, be bunched so as to be positioned essentially entirely within the graft but may include only forward portions of such positioned in the sheath. Thus the wire 24a can be of the relatively straight form shown and have a significant extent project rearwardly out of the sheath and patient's body. In this embodiment, it is also possible to use a sheath of reduced diameter approaching even that of the wire. Furthermore, the wire may actually be moved relatively to a stationary sheath so as to project outwardly of the lead end of the sheath so as to firmly position the wire vis-a-vis the patent vessel portion 12 or even to initiate heating and thus reformation of the wire in this manner.

It should also be brought out that a procedure combining the techniques and constructions shown and described in the FIGS. 1–4 and FIGS. 5 and 6 embodiments may be used as when a graft to which the wire is attached only to its leading or proximal end is used. Therein the member 52 may be utilized and constructed to be hollow (tubular) such that the wire 24 or 24a can pass internally through it outwardly into the enlarged sheath head 50 through an opening (not shown) provided in the platform 54. Also this combined technique could also be of use when a bunched wire 24 or 24a is placed in the sheath head 50 yet further wire is desired to follow and as an aid in initially moving the wire bunch relative to the sheath to initiate position.

Turning now to FIGS. 7 and 8 of the drawing, the present process is shown in directing a constricted vessel 30 such that the constriction is forced to more natural or at least patent dimensions by the application of the techniques of the present invention. In such case, a wire 34 which may correspond to either the wire 24 or 24a of the previously explained embodiments may be utilized. Such wire 34 is positioned on one side of the constriction 32 by a sheath 36 which may be of smaller diameter than sheath 20 and thereafter heated to its martensite transformation point and then enabled to progressively reshape itself to its original coil form 38 so as to progressively force the walls of the vessel into an original or at least patent position. A length of graft material can also be used in conjunction with the process as shown in FIGS. 7 and 8.

It should be brought out that heating the wire in any of the above embodiments to its transformation temperature could be accomplished other than solely by conduction and convection from the body but by infrared radiation. Thus infrared waves could be directed at forward portions of the wire by known means so as to progressively heat and reform the wire. Also when the body temperature is not exclusively relied upon as the source of heat for the wire, its reformation temperature could be increased above body temperatures if necessary or desirable to achieve particular characteristics. Naturally, radiation heating could also be utilized in conjunction with the previously described embodiments. Also although the wire form has been illustrated in the form of side by side circular loops along the longitudinal coil extent, it should be brought out that the loops could extend back and forth longitudinally and progressively build up in a circular path to form the completed wire form (cylindrical).

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated the the scope of the appended claims.

What is claimed is:

1. The process of restoring the patency and/or reestablish continuity of a disrupted hollow body vessel a patient which includes a localized defect disposed intermediate proximal and distal patent vessel portions, comprising inserting at least the forward end of a shape-memory allow wire having a parent phase and a martensite phase and a temperature transformation point therebetween and which wire has been previously formed in its parent phase to form a longitudinally oriented coil of adjacent wire loops and then cooled to its martensite phase and reshaped to an alternate form before insertion along the interior of said vessel past said defect to a position adjacent the proximal patent vessel portion while maintaining the temperature of said wire below its martensite transformation point and thereafter permitting the forward portion of said wire to be warmed above its transformation point so as to initially cause said alternate form to substantially revert to said parent phase coil form and to cause the thus reformed wire loops of the forward wire end to be urged against the interior of said proximal patent vessel portion so as to be at least temporarily positioned thereat and thereafter permit the reformation of the remainder of said coil so as to bridge said localized defect and extend into said distal patent vessel portion, said warming being progressive in the proximal to distal direction.

2. The process of claim 1, said reformed wire loops being substantially circular.

3. The process of claim 1 wherein the martensite transformation temperature of said wire is below the normal temperature range of said body.

4. The process of claim 3 wherein said wire in composed of a Nitinol alloy.

5. The process of claim 1 wherein said warming of said wire takes place by said body.

6. The process of claim 1 wherein the temperature of said wire is regulated by insulating means when initially inserted into said vessel.

7. The process of claim 6 wherein said insulating means is a tube through which said wire is transported to said proximal patent portion after which said tube is progressively withdrawn.

8. The process of claim 7 wherein a tubular graft is positioned over said wire in its alternate form prior to inserting said wire and said graft into said vessel.

9. The process of claim 8 wherein said wire is attached to said graft at least at the forward or proximal end thereof and said wire and graft are positioned in said tube in a crushed compacted form.

10. The process of claim 1 wherein the adjacent loops of said reformed coil are closely spaced to each other so as to essentially form the wall of the vessel in said defective portion thereof.

11. The process of claim 1 wherein a tubular graft is positioned over said wire in its alternate form prior to inserting said wire and said graft into said vessel.

12. The process of claim 1 wherein said wire is continuous.

13. The process of claim 1 wherein said alternate wire form is a substantially straight length thereof.

14. The process of claim 1, said alternate form of said wire being a crushed compacted form adapted for insertion into said body vessel.

15. The process of restoring the patency and/or reestablish continuity of a disrupted hollow body vessel of a patient which includes a localized defect disposed intermediate proximal and distal patent vessel portions, comprising inserting at least the forward end of a shape-memory alloy wire having a parent phase and a martensite phase and a temperature transformation point therebetween which is somewhat below the body temperature of said patent and which wire which has been previously formed in its parent phase to form a longitudinally oriented coil of adjacent wire loops and then cooled to its martensite phase and reshaped to an alternate form before insertion along the interior of said vessel past said defect to a position adjacent the proximal patent vessel portion while maintaining the temperature of said wire below its martensite transformation point and thereafter permitting said wire to be progressively warmed in the proximal to distal direction by the patient's body above its transformation point so as to initially cause said alternate form to substantially revert to said parent phase coil form and to cause the thus reformed wire loops of the forward wire end to be urged against the interior of said proximal patent vessel portion so as to be a least temporarily positioned thereat and thereafter permit the reformation of the remainder of said coil so as to bridge said localized defect and extend into position adjacent said distal patent vessel portion.

* * * * *